United States Patent [19]

Bürk

[11] Patent Number: 5,646,116

[45] Date of Patent: Jul. 8, 1997

[54] COMPOSITION AND METHOD FOR THE TREATMENT OF OSTEOPOROSIS IN MAMMALS

[75] Inventor: Robert Roland Bürk, Bottmingen, Switzerland

[73] Assignee: Ciba-Geigy AG, Basel, Switzerland

[21] Appl. No.: 396,884

[22] Filed: Mar. 1, 1995

Related U.S. Application Data

[63] Continuation of Ser. No. 252,061, Jun. 1, 1994, abandoned, which is a continuation of Ser. No. 990,821, Dec. 14, 1992, abandoned, which is a continuation of Ser. No. 686,309, Apr. 16, 1991, abandoned, which is a continuation of Ser. No. 460,416, Jan. 3, 1990, abandoned.

[51] Int. Cl.$^6$ .................................................. A61K 38/30
[52] U.S. Cl. .............................. 514/12; 514/21; 520/399
[58] Field of Search ........................................... 514/12

[56] References Cited

FOREIGN PATENT DOCUMENTS

| 0123228 | 1/1984 | European Pat. Off. . |
| 0123228 | 10/1984 | European Pat. Off. . |
| 0 289 314 A2 | 2/1988 | European Pat. Off. . |
| 0318184 | 5/1989 | European Pat. Off. . |

OTHER PUBLICATIONS

Hock, Chem. Abst. 88, 14 (1988), abst. No. 50024e.
Stedman's Medical Dictionary, 24th ed., Williams & Wilkins, Baltimore, 1982, p. 1301.
Chiron Corporation Annual Report 1987 (1–page).
Journal of Bone and Mineral Res., vol. 6, Suppl 1 Abstr. 549 p. F–221, Aug. 1991.
Endocrinology, 123, No. 1 373–381 (1988).
J. Biological Chem. 263, No. 13, 6233–6239 May 5, 1988.
Biochem and Biophys. Res. Comm. 165, No. 2 766–771, 1989.
Proc. Natl. Acad. Sci., 83 4904–4907, 1986.
Biochem. and Biophys. Res. Comm. 149 No. 2 398–404, 1987.
Biochem. and Biophys. Res. Comm. 149 No. 2 pp. 672–679, 1987.
J. Biological Chemistry, 261, No. 13 5693–5695, May 5, 1986.
Proc. Natl. Acad. Sci. 85 4889–4893, Jul. 1988.
New England Journal of Medicine 318, 818–823 Mar. 31, 1988.
Pediatric Research 20, No. 9 825–827, 1986.
Endocrinology 116, No. 6 2563–2567, 1985.
Am. J. Physiol 250:E367–E372, 1986.
J. Clin Endocrinol and Metab, 701–704 1984.
Mayo Clin Proc. 60:827–835, 1985.
J. Clin. Invest 66, 709–719, Oct. 1980.
Metabolism 26 No. 10 Oct. 1977, 1079–1087.
J. Clin. Endocrinol. and Metab, 65 No. 4 697–702, 1987.
Annals of Internal Medicine, 1984 100:908–911.
Annals of Internal Medicine, 1986 104:874–876.
"Comparison of in vivo effects of insulin–like growth factors I and II and of growth harmone in hypophysectomized rats", Schoenle et al. ACTA Endocrinologica 1985–106–167–174 (Abstract).

"Insulin–Like Growth Factors Stimulate Synthesis of Nucleic Acids and Glycogen in Cutured Calvaria Cells", Schmid et al (Alcif Tissue Int. (1983) 35:578–585.
Johansson et al, The Lancet, vol. 339: Jun. 27, 1992 p. 1619. Insulin–Like Growth Factor I stimulates bone turnover in osteoporosis.
Ebling et al; Journal of Bone and Mineral Research, vol. 7, Supp. 1, Aug. 1992, Short–Term Effects of Recombinant Human Insulin–Like Growth Factor–I in Bone Turnover in Normal Women.
Schoenle et al, Comparison of in–vivo effects of Insulin–like Growth Factors I and II . . . , Acta Endocrinologica (1985) 106:167–114.
Schmid et al, Insulin–like Growth Factors Stimulate Synthesis of Nucleic Acids . . . , Calcif. Tissue Int. 35:578–585 (1983).
Mueller et al., Insulin–like Growth Factor–I increases Trabecalo Bone Mass in Ovariectomized Rat, J. Bone Mineral Res. vol. 6, Supp. 1, F–221, Abstract #549 (1991).
Bennett et al, Characterization of Insulin–like Growth Factor I Receptors on Cultured Rat Bone Cells: . . . , Endocrinology v. 115, No. 4, 1577–158 1984.
Schwander et al, Synthesis and Secretion of Insulin–like Growth Factor . . . , Endocrinology vol. 113, No. 1, 297–305 (1983).
Simpson, Growth Factors which affect Bone, Physiol. 235 TIBS Dec. 1984.
Hologic QDR™–1000 Product Literature.
Annals of Internal Medicine 1984, v. 100, pp. 908–911 Radiologic Methods to Evaluate Bone Mineral Content.
Goffredsen et al, Total body bone mineral in vivo by dual photon absorptiometry, Clinical Physiology (1984) 4:343–355.
Wahner, Assessment of Metabolic Bone Disease Mayo Clin Proc 60:827–835, 1985.
Genant, et al, Osteoporosis:Assessment by Quantitative Computerized Tomography.
"Insulin–Like Growth Factor–1 Increases Trabecular Bone Mass in the Ovariectomized Rat". Mueller et al., J. Bone Mineral Res., Aug. 1991, vol. 6, Suppl. I Abstract 549 p. F–221.
Rote Liste, Editio Cantor, Aulendorf/Wurtt. 1988 Nos. 65–002–65–006–and 75,086.
Humbel, Rene E., (1990) "Insulin–Like Growth Factors I and II" Eur. J. Biochem. 190:445–462.
Merimee, Thomas J., (1987) "Insulin–Like Growth Factors in Pygmies" The New England Journal of Medicine 316(15):906–911.

Primary Examiner—Howard E. Schain
Attorney, Agent, or Firm—Roberta L. Robins; Amy L. Collins; Robert P. Blackburn

[57] ABSTRACT

A composition for the treatment of osteoporosis and the method of treatment of osteoporosis therewith in mammals is disclosed. The method comprises administering Insulin-Like Growth Factor I (IGF-I) to a mammal in need thereof. Need is determined by bone mineral density levels, whether by single measurement (as compared to the population generally) or by a series of measurements evidencing a loss of bone mineral density, or due to a genetic or familial or other predisposition to bone mineral density loss.

13 Claims, 6 Drawing Sheets

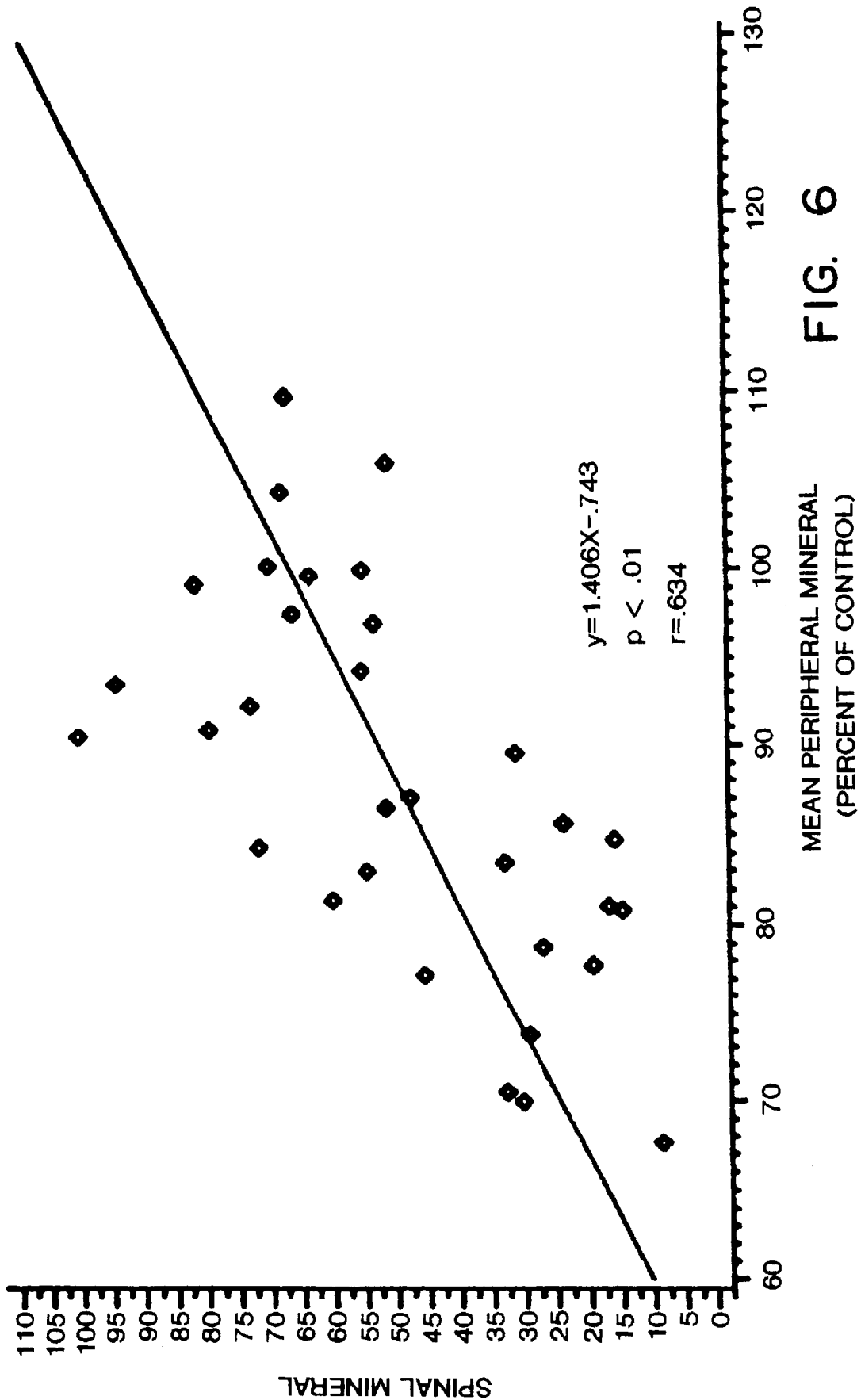

5,646,116

COMPOSITION AND METHOD FOR THE TREATMENT OF OSTEOPOROSIS IN MAMMALS

This application is a continuation of application Ser. No. 08/252,061 filed on 01 Jun. 1994, which is a continuation of application Ser. No. 07/990,821 filed 14 Dec. 1992, which is a continuation of application Ser. No. 07/686,309 filed 16 Apr. 1991, which is a continuation of application Ser. No. 07/460,416 filed 3 Jan. 1990, all now abandoned.

FIELD OF THE INVENTION

The present invention concerns a method for the treatment of patients having osteoporosis in which such patients exhibit decreased bone mineral density and patients substantially at risk of developing such decreased bone mineral density through the administration of insulin-like growth factor I (IGF-I) and pharmaceutical compositions therefore.

BACKGROUND OF THE INVENTION

Osteoporosis encompasses a broad range of clinical syndromes having varying etiologies. In postmenopausal women, for example, two distinct types of osteoporosis have been identified. Type I osteoporosis occurs mainly in the early postmenopausal period from about age 50–65. It is characterized by excessive resorption, primarily in trabecular bone. Vertebral fractures are common and if given prior to significant bone loss, treatment which decreases or prevents bone resorption (such as estrogen or calcitonin) is considered effective therapy.

Type II osteoporosis (a.k.a. senile osteoporosis) occurs essentially in all aging women and, to a lesser extent, in men. It is characterized by proportionate loss of conical and trabecular bone. Here decreased bone formation plays a major role, if not a more important role than increased bone resorption. Fractures of the hip are characteristic of this type.

Currently approved therapeutic agents for osteoporosis are antiresorptives. As such, they are not as effective in patients with established osteoporosis of either type (decreased bone density with fractures of the vertebrae and/or hip), or in patients with Type II osteoporosis. In addition, the most accepted preventive agent for osteoporosis currently in use is estrogen therapy, which is not really an acceptable therapeutic agent for women with a history of breast cancer or endometrial cancer or for men with osteoporosis.

Insulin-like Growth Factor I (IGF-I) is a 70 amino acid peptide belonging to a family of compounds under the class name somatedins and retains structural and biological similarities to insulin. The somatedins' activity lie on a spectrum from hypoglycemic effects similar to insulin to growth promoting effects which are exemplified by growth hormone. IGF-I predominantly induces growth and cell proliferation. IGF-I has also been demonstrated to specifically bind to receptors on rat osteoblast-like bone cells (Bennett et al, Endocrin. 115 (4): 1577–1583, 1984). IGF-I is routinely fabricated in the liver and released for binding to carrier proteins in the plasma (Schwander et al, Endocrin. 113 (1): 297–305, 1983), which bound form is inactive. In addition, there is a biofeedback regulating loop involving the somatomedins and growth hormone such that higher somatomedin concentrations inhibit growth hormone release which results in lesser production of endogenous IGF-I.

IGF-I infused into rats has been shown to result in markedly greater increases in body weight gain compared to controls, with increases in tibial epiphyseal width and thymidine incorporation into costal cartilage (Nature 107: 16–24, 1984) and directly stimulate osteoblasts to result in a greater number of functional osteoblasts. IGF-I is also mentioned as the vehicle through which growth hormone's effects on bone is mediated in Simpson, Growth Factors Which Affect Bone, Physiol. 235, TIBS, 12/84.

Nevertheless, it is important to note that the foregoing pre-clinical studies were conducted with fetal or newborn rat cells. It is highly likely that such "young" cells are more responsive to IGF-I (as well as other influences) than older cells, especially those in the elderly with established osteoporosis or those with drug or environmentally induced defects leading to reduced bone density.

Surprisingly, IGF-I has now been found to be useful in the treatment of osteoporosis in mammals exhibiting decreased bone mineral density and those exposed to drugs or environmental conditions which tend to result in bone density reduction and potentially to an osteoporosis condition.

Accordingly, an object of the present invention is to provide a method of treatment of osteoporosis in mammals exhibiting decreased bone mineral density and preventing osteoporosis due to bone mineral density reduction in patients who are clinically prone to such bone mineral density reductions.

Another object of the invention is to provide pharmaceutical compositions useful in achieving the foregoing object.

SUMMARY OF THE INVENTION

The present invention is directed to a method for, and composition useful in, the treatment of osteoporosis in patients demonstrating bone mineral density reductions and preventing such osteoporosis in patients prone thereto by administering to a patient having such osteoporosis or prone thereto an effective amount of IGF-I.

BRIEF DESCRIPTION OF THE DRAWINGS

FIGS. 1 and 2 are taken from the Mayo Clin. Proc., Vol. 60, Dec. 1985 reference mentioned above and are themselves based on data from Riggs B L, Wahner H W, Dunn W L, Mazess R B, Offord K P, Melton L J III: Differential changes in bone mineral density of the appendicular and axial skeleton with aging: relationship to spinal osteoporosis. J. Clin. Invest. 67: 328–335, 1981.

FIG. 6. Idiopathic osteoporotic male values showing larger decrement from normal for vertebral mineral QCT than for mean peripheral cortical mineral by radiogrammerry and photon absorptiometry.

FIGS. 3–6 are taken from Orthopedic Clinics of North America, Vol. 16. No. 3, July 1985 reference mentioned above.

Figure 1:
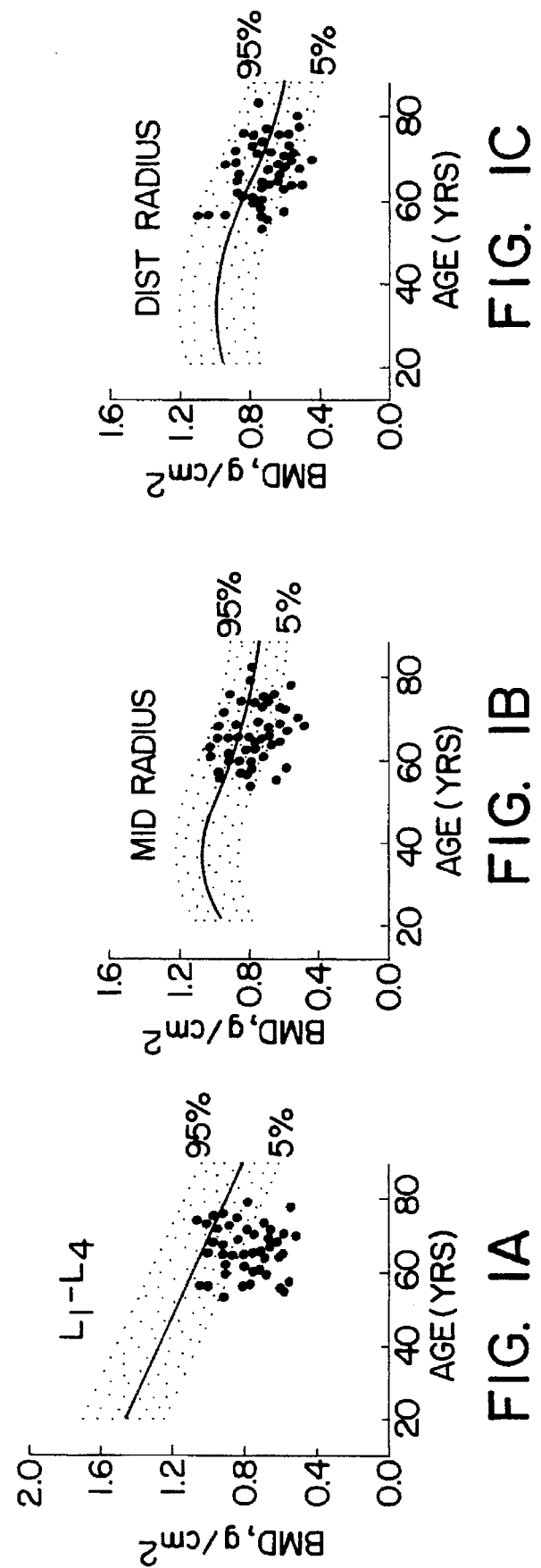
FIG. 1. Bone mineral density (BMD) in spine (L1-4; measured with use of dual-photon absorptiometry), midradius, and distal radius (measured with use of single-photon absorptiometry) in 76 women with osteoporosis in comparison with age- and sex-adjusted normal range (105 women). Shaded area represents 5th and 95th percentile range of normals. Patients with osteoporosis are indicated by dots. Note imcomplete separation of the two populations. Spinal measurements results in the best distinction of patients with osteoporosis from normal subjects because this disease primarily affects trabecular bone of the spine.
Figure 2:
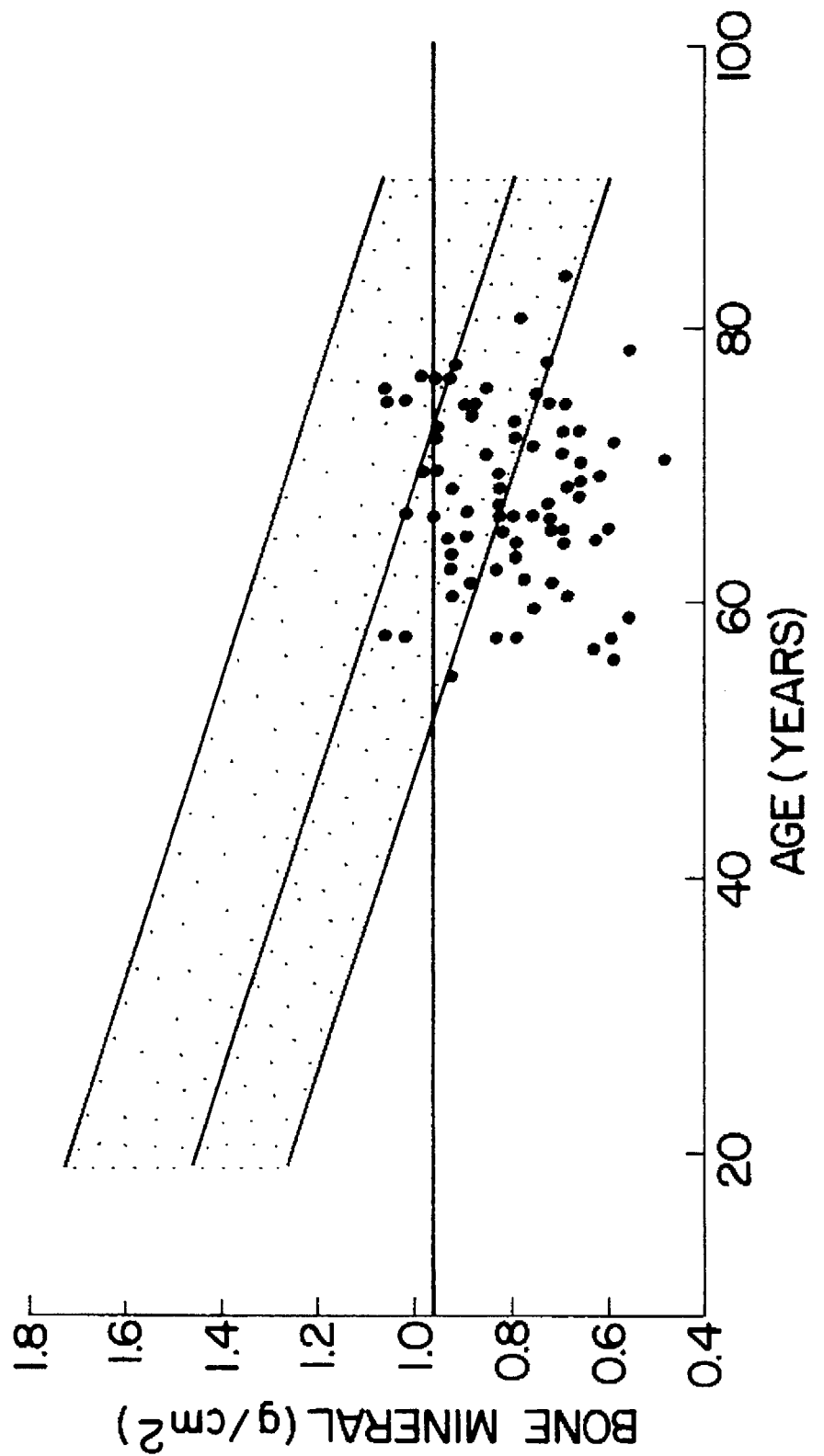
FIG. 2. Fracture threshold for spinal bone mineral (horizontal line) superimposed on normal range (shaded area) and values for 76 patients with osteoporosis (dots), as depicted in FIG. 1. With progressing age, values of increasing numbers of normal subjects are below the fracture threshold. Fracture threshold is approximately two standard deviations below mean bone mass at age 35 years.
Figure 3A:
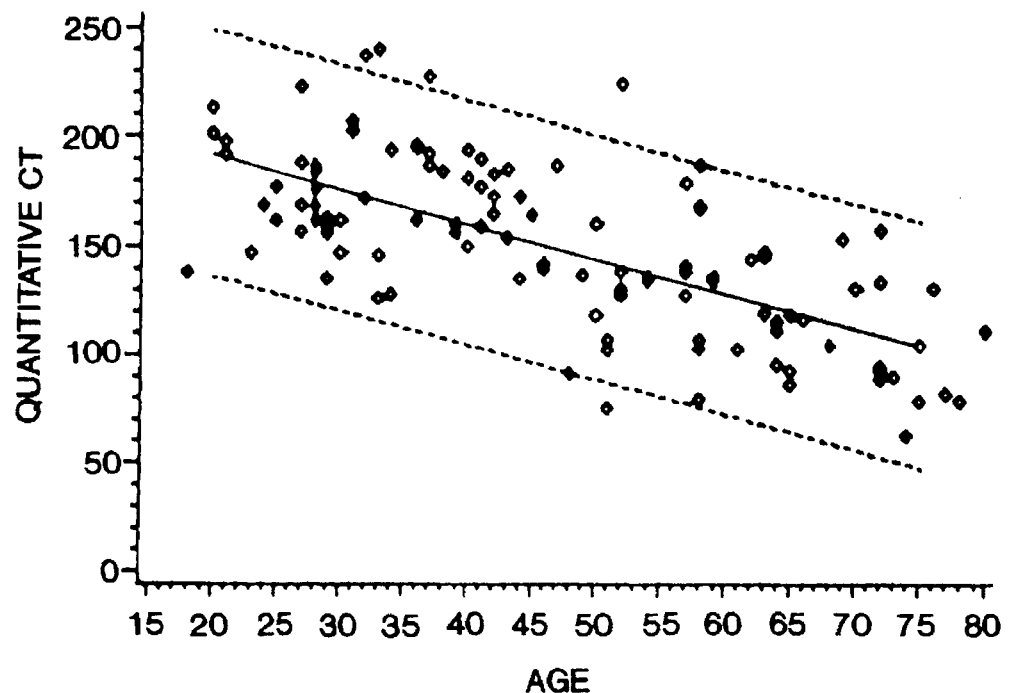
FIG. 3. A. Normal male values for vertebral cancellous mineral content by QCT, using a cubic regression with 95 percent confidence intervals. The cubic regression gives only a slightly better fit to the data for men than does a linear regression (p.<0.15). B. Normal female values for vertebral cancellous mineral content by QCT, using a cubic regression with 95 per cent confidence intervals (p.<0.05). An accelerated loss is observed after menopause.
Figure 3B:
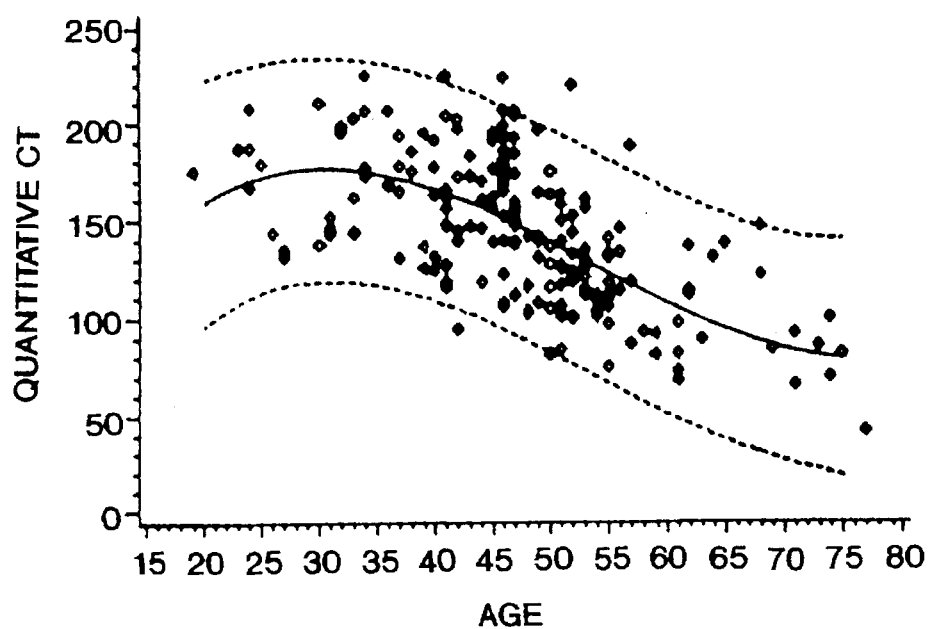
Figure 4A:
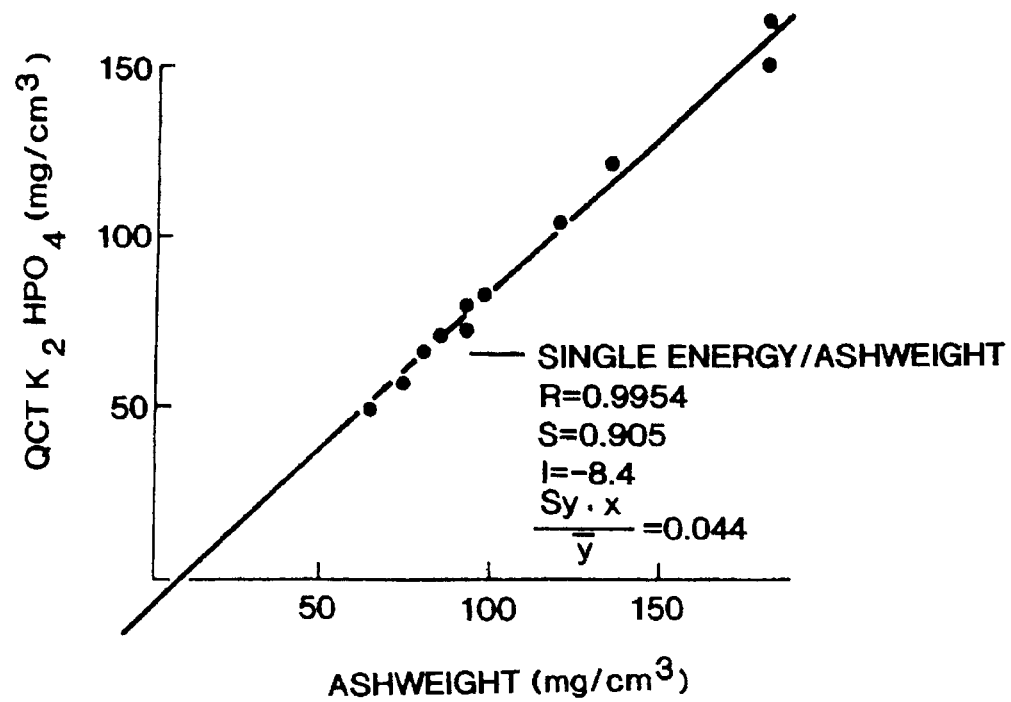
FIG. 4. A and B. The accuracy of single-energy QCT is shown for vertebral specimens (preserved in sodium azide) from 11 patients (10 men and 1 women), ages 40 to 90 years.
Figure 4B:
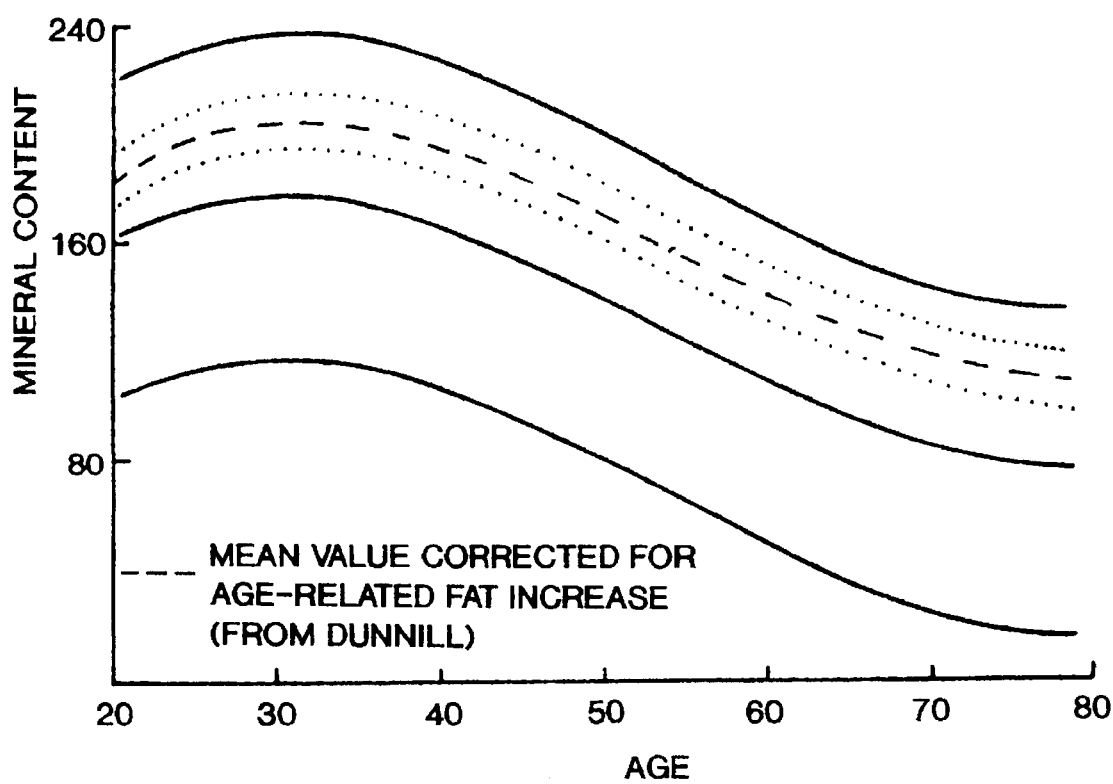
Figure 5:
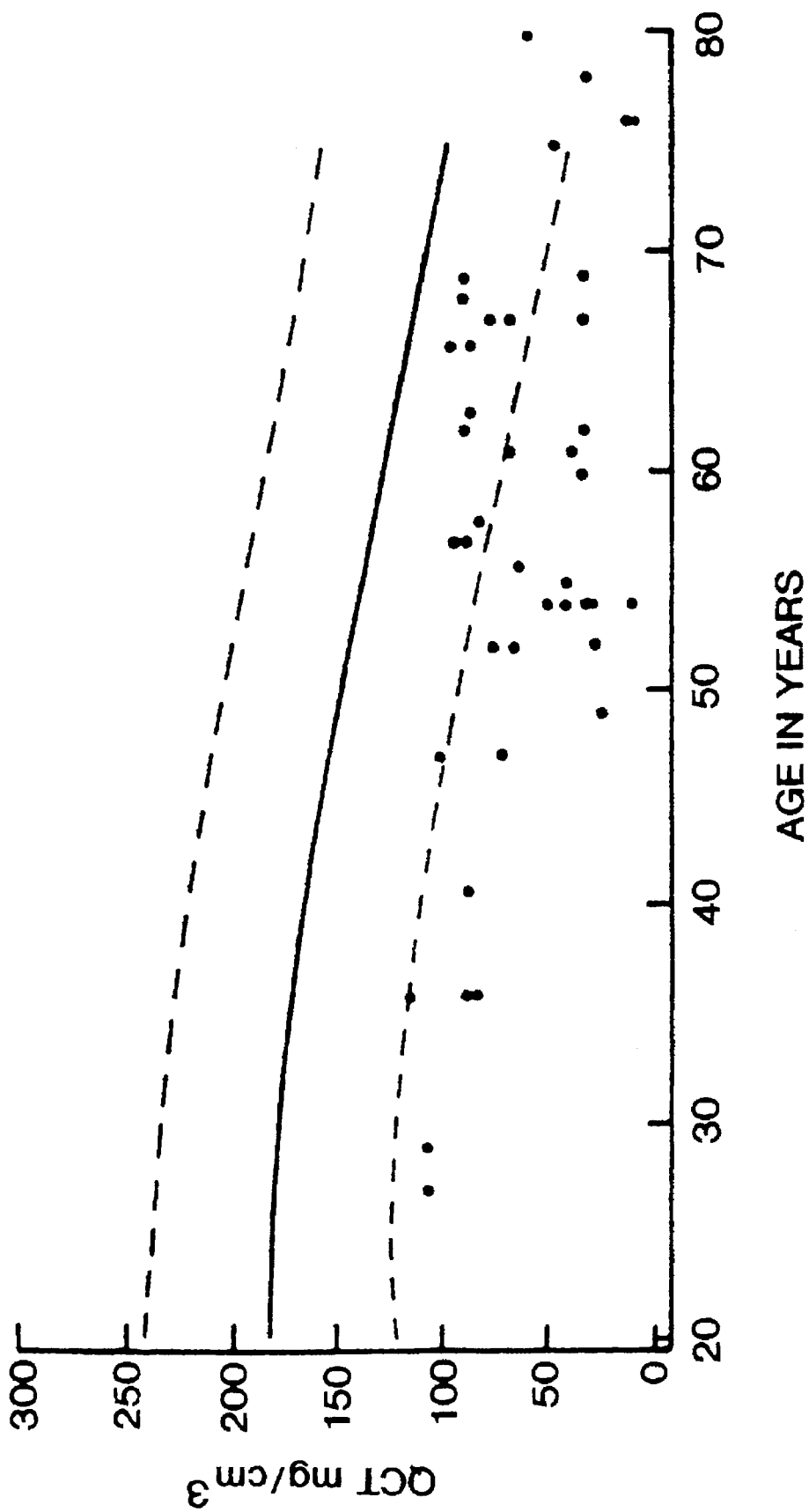
FIG. 5. Values for men with idiopathic osteoporosis and spinal fractures are plotted (black dots) against the normal male curve (cubic regression with 95 per cent confidence intervals). A fracture threshold at approximately 110 mg/cm$^3$ is observed.

Having fully described the instant invention, the following non-limiting Examples are presented to more clearly set forth the invention without limiting it.

DETAILED DESCRIPTION OF THE INVENTION

The present invention concerns osteoporosis treatment and prevention, which osteoporosis is associated with decreased bone mineral density in mammals generally, but is especially suited for the treatment and prevention of such osteoporosis in humans.

IGF-I is a naturally occurring protein and can be obtained from a number of sources. Preferably, IGF-I from the same species, (or its synthetic twin) as is being treated therewith is employed but IGF-I from one species may be used to treat another species if the immune response elicited is slight or nonexistent. In addition, fragments of IGF-I having IGF-I activity, particularly IGF-I antiosteoporosis activity, are also suitably employed and unless the context of the disclosure clearly indicates otherwise, IGF-I as used herein is intended to include such active fragments. Where weights of IGF-I are presented, that weight of IGF-I and an approximately equipotent amount of active fragments is intended unless the text explicitly states otherwise. Where no type of IGF-I is indicated, reference is to human -IGF-1 (meaning the structure, not the species source), unless the reasonable reading of the text indicates otherwise.

IGF-I can be synthetically produced, chemically or by recombinant techniques, although recombinant preparation is preferred. One such recombinant technique is disclosed in EP 123,228, incorporated herein by reference.

An effective amount of IGF-I is an amount sufficient to slow, stop, or reverse the bone mineral density reduction rate in a patient exhibiting bone mineral density reduction. In the Normal healthy 20–25 year old population bone mineral density in the spine (using dual photon densitometry) typically is in the range of 0.85 to 1.9 g/cm, usually 0.9 to 1.85 and most often 1.0 to 1.8; and in the mid radius and distal radius it is typically 0.7–1.4, usually 0.75–1.3, and most often 0.8–1.2 g/cm$^2$. Exemplary non-limiting normal ranges are shown in the Figures along with osteoporosis distributions. Norms using other techniques will be apparent from the literature and general experience therewith as experience with such techniques grow. Of course, it is to be remembered that different sub-populations have different norms in bone mineral density. For example caucasian women typically differ in this parameter from caucasian men as well as from black women, oriental women and women of other racial types. It is also important to remember that the current invention is directed to treating those with bone mineral density which is (a) totally below either the normal bone mineral density range for the population generally or for the patient sub-population or (b) below 1.0 g/cm$^3$ or (c) below the fracture threshold (approximately 2 standard deviations below the mean bone mass for the population at age 35). The fracture threshold for the spine for example is defined as the bone mineral value below which 90% of all patients with one or more compression fractures of the spine are found (See Mayo Clin. Proc., Dec. 1985, Vol 60, p. 829–830). In addition, anyone who demonstrated a statistically significant reduction in bone density over a previous measurement, regardless of where that patient is in the typical ranges above, is a patient to whom the present invention treatment is directed. Statistical significance in this context will vary with the technique employed to measure bone mineral density, as well as with the sensitivity of the instruments used. However, with instrumentation and techniques generally available in 1988, a 1 or 2% change in bone mineral density from the earliest measurement to the most recent is not considered statistically significant. Still as techniques and equipment improve, persons of ordinary skill in the field of bone density measurement will revise downward the maximum percent change which is not considered statistically significant.

Current bone mineral density measurement techniques include dual energy radiography, quantitative computerized tomography, single photon densitometry, and dual photon densitometry. These techniques will be well known to those of ordinary skill in the art; however, descriptions thereof can be found in: Mayo Clin. Proc., Dec. 1985, Vol. 60, p. 827–835; Orthopedic Clinics of North America, Vol. 16, No. 3, July 1985, p. 557–568; Hologic QDR™-1,000 Product Literature; Annals of Internal Medicine, 1984, 100: p. 908–911; and Clinical Physiol 4: 343, 1984.

Notwithstanding, the lack of statistical significance in a particular result, any bone mineral density reduction should be followed for further reductions, which cumulatively may be significant.

Usually, an effective amount of IGF-I, when given parenterally (intravenously, subcutaneously, intramuscularly, etc.), is between 2½ µg/Kg/day up to about 180 µg/Kg/day, preferably about 5 µg/Kg/day up to about 150 µg/KG/day, more preferably 10 µg/Kg/day up to about 120 µg/Kg/day, even more preferably 20 µg/Kg/day up to about 100 µg/Kg/day, still more preferably about 30 µg/Kg/day up to about 90 µg/Kg/day. When given continuously, such effective amount may be given in two or three doses spread over time such as by IV drip or subcutaneous injection(s) with the total daily dose being spread across the portion or the entire administration period. Typical continuous dosing is in the range of about 2½ µg/Kg/hour up to about 50 µg/Kg/hour, preferably about 5 µg/Kg/hour up to about 25 µg/Kg/hour, although wider ranges of "continuous" administration amounts will be apparent to those of ordinary skill. When given by subcutaneous injection, it is most preferably administered from 3 times/wk up to 3 times a day, preferably twice a week up to once or twice daily.

The specific dosage for a particular patient, of course, has to be adjusted to the degree of response, the route of administration, the individual weight and general condition of the patient to be treated, and is finally dependent upon the judgement of the treating physician.

In general the pharmaceutical preparations for use in the present invention comprise an effective amount of IGF-I or an active fragment thereof together with a pharmaceutically and parenterally acceptable carrier or adjuvant. Compositions having an approximately 6 day supply typically contain from 0.1 mg to 15 mg, preferably 1 mg to 13 mg, more preferably about 3 mg to about 10 mg, most preferably 5 mg-10 mg of IGF-I. The liquid carriers are typically sterile water, approximate physiologic saline, 0.1M acetic acid, 5% aqueous dextrose, etc.; preferably sterile water, physiologic saline, or 5% aqueous dextrose.

The carriers and adjuvants may be solid or liquid and may be organic or inorganic. The active compound and the compositions of the invention are preferably used in the form of preparations or infusions for parenteral (subcutaneous, intramuscular, or intravenous) administration. Such solutions are preferably isotonic aqueous solutions or suspensions which can be prepared before use, for example reconstituted from a lyophilised preparation. The pharmaceutical preparations may be sterilized and/or contain adjuvants, for example preservatives, stabilizers, wetting agents, emulsifiers, solubilizers, tonicity regulating salts, and/or buffers. Other adjuvants will of course be apparent to the ordinarily skilled formulation chemist.

The present pharmaceutical preparations, which, if desired, may contain further pharmacologically active or otherwise pharmaceutically valuable substances, especially bone antiresorptives such as estrogen, calcitonin, and bisphosphonates particularly 3-aminopropyl-1-hydroxy-1,1-bisphosphonate are prepared from their constituent parts by techniques known in the art, for example lyophilization, dissolution, reconstitution, and suspension techniques, among others known to those of ordinary skill. They typically contain from about 0.1% to about 100% of active ingredient, especially in the case of solutions—about 1% to about 20% active ingredient and especially in the case of a lyophilizate—up to 100% of active ingredient.

EXAMPLES 1–3

Dry ampules of IGF-I

Sterile, filtered 1% (w/v) aqueous solution of IGF-I is added, in the amount indicated to the respective dry amules the solution is then lyophilized to result in the dry ampules to be reconstituted shortly before use with the indicated amount of sterile water, physiologic saline, 0.1M acetic acid, or 5% aqueous dextrose. Each vial is sufficient for a 6 day course of treatment for the intended patient.

|  | Ex 1 | Ex 2 | Ex 3 |
| --- | --- | --- | --- |
| ampule size | 5 ml | 8 ml | 50 ml |
| IGF-I fill volume | 1 ml | 5 ml | 30 ml |
| Reconstitution Volume | 1 ml | 5 ml | 30 ml |

What is claimed is:

1. A method for the treatment of osteoporosis in a mammal having reduced bone mineral density or prevention thereof in a mammal prone thereto comprising administering to said mammal in need thereof an effective amount for said treatment or prevention, respectively, of IGF-I.

2. The method of claim 1 wherein said mammal is a human being.

3. The method of claim 1 wherein said IGF-I is chemically the same as natural IGF-I from the same species as is said mammal receiving said treatment or preventive administration therewith.

4. The method of claim 1 wherein said IGF-I is naturally occurring IGF-I.

5. The method of claim 1 wherein said IGF-I is synthetically produced IGF-I.

6. The method of claim 1 wherein said IGF-I is produced by recombinant techniques.

7. The method of claim 1 wherein said administration is parenterally.

8. The method of claim 1 wherein said reduction in bone mineral density in said mammal is in excess of 2% of a previous bone mineral density measurement in said mammal.

9. The method of claim 8 wherein said reduction in bone density in said mammal is in excess of 4% of a previous bone density measurement in said mammal.

10. The method of claim 8 wherein said reduction in bone mineral density in said mammal is in excess of 6% of a previous bone mineral density measurement in said mammal.

11. The method of claim 1 wherein said reduced bone mineral density is characterized as being at or below the lower 10th percentile of the general population of mammals of the same species between the ages of 1½ times and 2 times reproductive maturity for said species.

12. The method of claim 11 wherein said reduced bone mineral density is characterized as being at or below the lower 10th percentile of the racial, sexual, or both racial and sexual subpopulations of mammals of the same species between the ages of 1½ times and 2 times reproductive maturity for said species.

13. The method of claim 11 wherein said mammal is a human being and said 1½ times to 2 times reproductive maturity is the age bracket of 20–25 years.

* * * * *